United States Patent
Sone et al.

(10) Patent No.: US 9,757,017 B2
(45) Date of Patent: Sep. 12, 2017

(54) ENDOSCOPE PROVIDED WITH A PLURALITY OF ILLUMINATION OPTICAL SYSTEMS

(71) Applicant: OLYMPUS CORPORATION, Hachioji-shi, Tokyo (JP)

(72) Inventors: Nobuhiko Sone, Tokyo (JP); Hideyasu Takato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/234,566

(22) Filed: Aug. 11, 2016

(65) Prior Publication Data

US 2016/0345811 A1 Dec. 1, 2016

Related U.S. Application Data

(63) Continuation of application No. PCT/JP2015/071556, filed on Jul. 29, 2015.

(30) Foreign Application Priority Data

Aug. 22, 2014 (JP) ................. 2014-169407

(51) Int. Cl.
*A61B 1/06* (2006.01)
*A61B 1/00* (2006.01)

(52) U.S. Cl.
CPC ............. *A61B 1/0607* (2013.01); *A61B 1/00* (2013.01); *A61B 1/00096* (2013.01); *A61B 1/0676* (2013.01); *A61B 1/06* (2013.01)

(58) Field of Classification Search
CPC ......... A61B 1/06; A61B 1/07; A61B 1/00096; A61B 1/0607; A61B 1/0676; G02B 23/2423; G02B 23/2461
See application file for complete search history.

(56) References Cited

U.S. PATENT DOCUMENTS

2001/0003142 A1 6/2001 Koshikawa
2006/0052668 A1* 3/2006 Homma ............... A61B 1/07
600/177

(Continued)

FOREIGN PATENT DOCUMENTS

JP 2001166223 A 6/2001
JP 2007249189 A 9/2007

(Continued)

OTHER PUBLICATIONS

International Search Report (ISR) and Written Opinion dated Oct. 27, 2015 issued in International Application No. PCT/JP2015/071556.

(Continued)

*Primary Examiner* — John P Leubecker
(74) *Attorney, Agent, or Firm* — Holtz, Holtz & Volek PC

(57) ABSTRACT

This endoscope has an observation optical system provided in a distal end of an inserted portion of the endoscope, for observation of an object, and plural illumination optical systems provided in the inserted portion, for illuminating a certain angle of view, wherein one illumination optical system having the widest light distribution is distant from the observation optical system relative to another illumination optical systems having the narrowest light distribution, and the following conditional expression is satisfied, $$0.6 \leq |\phi_S \cdot f_W / \phi_W \cdot f_S| \leq 1.0 \quad (1)$$

wherein $f_W$ is a focal length of the widest light distribution optical system, $f_S$ is a focal length of the narrowest light distribution optical system, $\phi_W$ is an outer diameter of the lens nearest to the object within the widest light distribution optical system, and $\phi_S$ is an outer diameter of the lens nearest to the object within the narrowest light distribution optical system.

7 Claims, 5 Drawing Sheets

(56) References Cited

U.S. PATENT DOCUMENTS

| | | | |
|---|---|---|---|
| 2007/0055106 A1* | 3/2007 | Moriyama | A61B 1/00096 600/178 |
| 2009/0048490 A1* | 2/2009 | Iijima | A61B 1/00096 600/180 |
| 2012/0245421 A1 | 9/2012 | Kitano | |
| 2013/0310649 A1 | 11/2013 | Sone | |
| 2014/0081085 A1* | 3/2014 | Takato | A61B 1/00096 600/129 |
| 2015/0257630 A1* | 9/2015 | Sone | A61B 1/00 600/109 |
| 2016/0256042 A1* | 9/2016 | Takato | G02B 23/26 |
| 2016/0367113 A1* | 12/2016 | Katakura | A61B 1/00096 |
| 2017/0052359 A1* | 2/2017 | Katakura | A61B 1/00 |

FOREIGN PATENT DOCUMENTS

| | | |
|---|---|---|
| JP | 2009022375 A | 2/2009 |
| JP | 2012047909 A | 3/2012 |
| JP | 2012196307 A | 10/2012 |
| JP | 5075658 B2 | 11/2012 |
| WO | 2013080831 A1 | 6/2013 |

OTHER PUBLICATIONS

Decision to Grant a Patent dated May 10, 2016 issued in counterpart Japanese Application No. 2016-506025.

* cited by examiner

| ANGLE $\alpha$ | ILLUMINANCE $\gamma_{LG}(\alpha)$ |
|---|---|
| 0 | 1.00 |
| 5 | 0.97 |
| 10 | 0.94 |
| 15 | 0.85 |
| 20 | 0.67 |
| 25 | 0.46 |
| 30 | 0.27 |
| 35 | 0.13 |
| 40 | 0.05 |
| 45 | 0.01 |
| 50 | 0.00 |
| 55 | 0.00 |
| 60 | 0.00 |
| 65 | 0.00 |
| 70 | 0.00 |
| 75 | 0.00 |

FIG. 7

ENDOSCOPE PROVIDED WITH A PLURALITY OF ILLUMINATION OPTICAL SYSTEMS

CROSS-REFERENCE TO RELATED APPLICATIONS

This application is a Continuation application of International Application No. PCT/JP2015/071556 filed on Jul. 29, 2015, which claims priority to Japanese Application No. 2014-169407 filed on Aug. 22, 2014.

The Contents of International Application No. PCT/JP2015/071556 and Japanese application No. 2014-169407 are hereby incorporated herein by reference in its entirety.

TECHNICAL FIELD

The present invention relates to an endoscope, and more particularly to an endoscope provided with a plurality of illumination optical systems at the insertion portion of the tip.

BACKGROUND ART

In general, the distal end portion of an endoscope is provided with components, such as an illumination optical system for radiating illumination light to an object, an observation optical system for observation of the object, a channel for guiding a treatment instrument and etc., a nozzle for cleaning the lens surface of the observation optical system, and the like. Further, an endoscope which is capable of efficiently illuminating a field of view having a wide angle of view by providing a plurality of the illumination optical systems has also been proposed. As such endoscopes, for example, PTL 1 discloses an endoscope which has an observation window of an observation optical system, a forceps opening whose diameter is larger than that of the observation window, and a plurality of illumination windows for radiating illumination, which are located in the distal end surface of the inserted portion. The plurality of illumination windows are located so that the observation window is located between the illumination windows, the illumination angle and light distribution of the illumination optical system disposed at position adjacent to the observation optical system is wide.

CITATION LIST

Patent Literature

{PTL 1} Japanese Unexamined Patent Application, Publication No. 2007-249189
{PTL 2} Japanese Patent No. 5075658

SUMMARY OF INVENTION

One aspect of the present invention provides an endoscope comprising: an observation optical system provided in a distal end of an inserted portion of the endoscope, for observation of an object; and a plurality of illumination optical systems which are provided in the inserted portion and which direct illumination light radiated from a light source toward the object so that the same angle of view is irradiated by the plurality of illumination optical systems, wherein one of illumination optical systems which has the widest light distribution is distant from the observation optical system relative to another one of the illumination optical systems which has the narrowest light distribution, and the following conditional expression is satisfied.

$$0.6 \leq |\phi_S \cdot f_W / \phi_W \cdot f_S| \leq 1.0 \tag{1}$$

In the expression, $f_W$ is a focal length of the illumination optical system which has the widest light distribution, $f_S$ is a focal length of the illumination optical system which has the narrowest light distribution, $\phi_W$ is an outer diameter of a lens at a position which is the nearest to the object within the illumination optical system having the widest light distribution, and $\phi_S$ is an outer diameter of a lens at a position which is the nearest to the object within the illumination optical system having the narrowest light distribution.

DESCRIPTION OF EMBODIMENTS

Embodiment

An endoscope according to an embodiment of the present invention will be described below with reference to the drawings.

Figure 1:
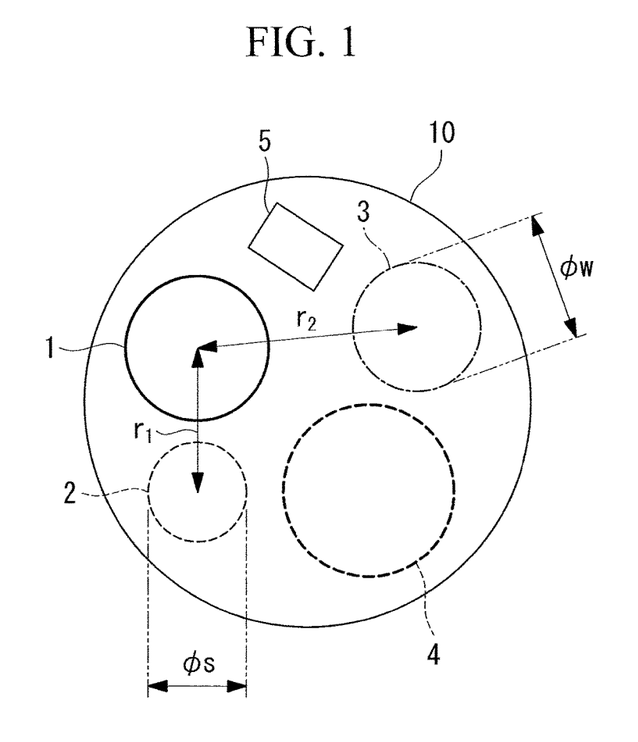
FIG. 1 is a drawing for explanation showing a distal end surface of an inserted portion of an endoscope according to an embodiment of the present invention.

FIG. 1 shows a distal end surface 10 of an inserted portion of the endoscope according to this embodiment. As shown in FIG. 1, the endoscope has an observation optical system 1 for observation of an object, a plurality of illumination optical systems 2, 3 for illuminating the same angle of view by distributing light radiated by a light source, which is not shown in the drawings, to the object, a channel 4 through which a treatment instrument, such as forceps or the like is able to come out, and a nozzle 5 for cleaning dirt or the like adhering to a lens, such as one of the lenses between the illumination window and the observation window, which are located at the distal end of the inserted portion.

In this embodiment, as the plurality of illumination optical systems, the endoscope has two illumination optical systems 2, 3 each of which has a light distribution characteristic which is different from each other and each of which has a distance from the objective optical system 1 which is different from each other. As shown in FIG. 1, the illumination optical system 3 disposed at a position which is more distant from the objective optical system 1 than the illumination optical system 2 is a illumination optical system which has a wider light distribution than that of the illumination optical system 2.

Thus, the illumination optical system 2 which has a narrow light distribution is located at a position whose distance from the center of the objective optical system 1 is r1, and the illumination optical system 3 which has a wide light distribution is located at a position whose distance from the center is r2 (r1<r2).

Note that when the amount of light from the illumination optical system 2 is large or its light distribution is wide, flare caused by light directly going into the objective optical system 1 or halation that part of an observation image becomes too white because of strong light irradiated on the periphery when approaching to the object, caused by a situation where the amount of light at the periphery becomes large, and the like, which are optically undesirable phenomena, are caused frequently. Thus, in order to achieve illumination with less flare and halation with regard to the illumination optical system 2 disposed at a position near the objective optical system 1, it is necessary to make the amount of light from the illumination optical system 2 small, and to make the light distribution relatively narrow. In other words, it is necessary to make the focal length long, and to make the outer diameter of the lens small.

However, when the aforementioned configuration is employed, the amount of light at a distant point becomes insufficient, and therefore the light distribution at the periphery of the image becomes insufficient. Thus, it is necessary to make the amount of light from the illumination optical system 3, which is located at the distant side in the plurality of illumination optical systems 2, large, and to make the light distribution wide. In other words, the focal length should be shortened, and the outer diameter of the lens should be enlarged. Thus, the illumination optical system 2 with a narrow light distribution and the illumination optical system 3 with a wide light distribution are located to satisfy the following conditional expression (1).

$$0.6 \leq |\phi_S \cdot f_W / \phi_W \cdot f_S| \leq 1.0 \quad (1)$$

In the expression, $f_W$ is the focal length of the illumination optical system 3 which has the widest light distribution, $f_S$ is the focal length of the illumination optical system 2 which has the narrowest light distribution, $\phi_W$ is the outer diameter of the lens at a position which is the nearest to the object within the illumination optical system 3 which has the widest light distribution, and $\phi_S$ is the outer diameter of the lens at a position which is the nearest to the object within the illumination optical system 2 which has the narrowest light distribution.

When the conditional expression (1) is satisfied, it becomes possible to make the amount of light large, to make the light distribution wide, to suppress flare and halation, and therefore to achieve a desired observation.

If the condition exceeds the upper limit of the conditional expression (1), the light distribution of the illumination optical system 2, which is nearer to the observation optical system 1, becomes undesirably wide, and therefore undesirable phenomena, such as flare and halation tend to occur frequently. On the other hand, the condition does not reach the lower limit of the conditional expression (1), since one of the light distributions becomes undesirably wide, only the position where the illumination is located becomes bright, and unevenness arises by the illumination optical system in a state in which a portion of the image is bright, while it is suitable regarding flare and halation.

It is preferable to employ the following conditional expression (1') instead of the conditional expression (1), and also it is more preferable to employ the following conditional expression (1") instead of the conditional expression (1').

$$0.7 \leq |\phi_S \cdot f_W / \phi_W \cdot f_S| \leq 0.95 \quad (1')$$

$$0.75 \leq |\phi_S \cdot f_W / \phi_W \cdot f_S| \leq 0.92 \quad (1'')$$

Further, when the observation is performed approaching to the object, the influence from the illumination optical system 3 which is located at the distant side relative to the observation optical system 1 becomes weak, and the influence from the illumination optical system 2 which is located at the near side relative to the objective optical system 1 becomes large. Further, since the object generally tends to have a planer body when a close observation is performed, the observation becomes difficult due to directly reflected light from the object, and it becomes necessary to set the illumination optical system 2 in a proper way. Also, when approaching to the object, necessary irradiated area is largely influenced by the observation area which depends on the field of view of the observation optical system 1. For the reasons above, in order to provide an illumination optical system especially suitable for close observation, the illumination optical system 2 and the observation optical system 1 are configured to satisfy the following conditional expression (2).

$$1.6 \leq |\phi_S \cdot f_L / f_S \cdot \phi_L| \leq 2.8 \quad (2)$$

In the expression, $f_L$ is the focal length of the objective optical system 1, and $\phi_L$ is the maximum image height of the observation optical system 1.

When the conditional expression (2) is satisfied, the illumination becomes suitable for close observation. When the condition does not reach the lower limit of the conditional expression (2), it becomes impossible to conduct a desired observation due to undesirably narrow light distribution of the illumination optical system 2 and undesirably wide field of view of the observation optical system 1. When the condition exceeds the upper limit of the conditional expression (2), the field of view becomes too narrow, which is not desirable.

It is preferable to employ the following conditional expression (2') instead of the conditional expression (2), and also it is more preferable to employ the following conditional expression (2") instead of the conditional expression (2').

$$1.8 \leq |\phi_S \cdot f_L / f_S \cdot \phi_L| \leq 2.6 \quad (2')$$

$$2.0 \leq |\phi_S \cdot f_L / f_S \cdot \phi_L| \leq 2.4 \quad (2'')$$

When the plurality of illumination optical systems 2, 3, each of which has a light distribution different from each other, are located, by positioning the illumination optical system 3 having a wide light distribution so that the illumination optical system 3 is positioned farther relative to the observation optical system. 1 than the illumination optical system 2, it becomes possible to conduct a desired observation because the brightness at the time of close observation becomes even over the entire observation area, compared with a situation where the illumination optical systems 2, 3 are positioned at the same distance from the observation optical system 1. Then it is configured so that the following conditional expression (3) is satisfied.

$$1.0 \leq r_2/r_1 \leq 2.0 \tag{3}$$

In the expression, $r_1$ is the distance between the center of the observation optical system 1 and the center of the illumination optical system 2 having a narrow light distribution, and $r_2$ is the distance between the center of the observation optical system and the center of the illumination optical system 3 having a wide light distribution.

When the conditional expression (3) is satisfied, the brightness at the time of close observation becomes even over the entire observation area, and thereby a better observation becomes available. When the condition does not reach the lower limit of the conditional expression (3), only the direction to which the illumination having the wide light distribution is positioned is brightly irradiated, and thereby the brightness does not become even over the entire observation area. When the condition exceeds the upper limit of the conditional expression (3), it leads to an undesirable situation where the brightness is not even over the entire observation area. It is preferable to employ the following conditional expression (3') instead of the conditional expression (3).

$$1.2 \leq r_2/r_1 \leq 1.8 \tag{3'}$$

When trying to reduce halation, there is a fear that light distribution tends to be insufficient. Especially, when the distance between the observation optical system 1 and the illumination optical systems 2, 3 is changed, the influence also changes. Thus, with regard to the illumination optical systems 2, 3, it is desirable that the light distributions of them are respectively and appropriately set in accordance with the distances between the objective observation system 1 and the illumination observation systems 2, 3. Thus, in order to achieve a desired observation, it is configured so that the following conditional expressions (4) and (5) are satisfied.

$$12 \leq r_1^2/|f_S \cdot f_W| \leq 48 \tag{4}$$

$$24 \leq r_2^2/|f_S \cdot f_W| \leq 96 \tag{5}$$

When the conditional expressions (4) and (5) are satisfied, it becomes possible to conduct a desired observation. In both of the conditional expressions (4) and (5), when the condition does not reach each of the lower limits, since the light distribution becomes too wide, frequency of causing undesired phenomena, such as flare and halation, becomes high. On the other hand, when the condition exceeds each of the upper limits in the conditional expressions (4) and (5), the illumination optical system is located at a position which is distant from the objective optical system 1, and thereby sufficient light does not reach the observation area, or it becomes impossible to ensure sufficient brightness because of too narrow light distribution of the illumination optical systems 2, 3.

Also, in order to ensure sufficient brightness at the periphery in close observation, it is configured that the angle characteristics of the illumination optical system 2 having a narrow light distribution and the illumination optical system 3 having a wide light distribution satisfy the following conditional expression (6). In other words, when the conditional expression (6) is satisfied, since the light from the illumination optical system 3, which is located at the distant side, is sufficiently irradiated onto the observation area at the time of close observation, balanced brightness can be ensured, without unevenness.

$$\gamma_W(60)/\gamma_S(60) \geq 1.0 \tag{6}$$

In the expression, $\gamma_S(60)$ is a ratio of an amount of radiated light at a radiation angle of 60° of the illumination optical system having the narrowest light distribution relative to the amount of radiated light at the radiation angle of 0° of the illumination optical system having the narrowest light distribution, and $\gamma_W(60)$ is a ratio of an amount of radiated light at a radiation angle of 60° of the illumination optical system having the widest light distribution relative to the amount of radiated light at the radiation angle of 0° of the illumination optical system having the widest light distribution.

It is preferable to employ the following conditional expression (6') instead of the conditional expression (6), and also it is more preferable to employ the following conditional expression (6") instead of the conditional expression (6').

$$\gamma_W(60)/\gamma_S(60) \geq 1.15 \tag{6'}$$

$$\gamma_W(60)/\gamma_S(60) \geq 1.50 \tag{6"}$$

In order to enable a desired observation even when the distal end of the inserted portion of the endoscope and the object are distant from each other with a certain degree, it is configured that the angle characteristics of the illumination optical system 2 having a narrow light distribution and the illumination optical system 3 having a wide light distribution satisfy the following conditional expressions.

$$0.05 \leq \gamma_S(50) \leq 0.25 \tag{7}$$

$$0.10 \leq \gamma_W(50) \leq 0.30 \tag{8}$$

In the expression, $\gamma_S(50)$ is a ratio of an amount of radiated light at a radiation angle of 50° of the illumination optical system having the narrowest light distribution relative to an amount of radiated light at a radiation angle of 0° of the illumination optical system having the narrowest light distribution, and $\gamma_W(50)$ is a ratio of an amount of radiated light at a radiation angle of 50° of the illumination optical system having the widest light distribution relative to an amount of radiated light at a radiation angle of 0° of the illumination optical system having the widest light distribution.

When the condition does not reach the lower limit of the conditional expressions (7) and (8), observations become better when the distance between the distal end of the inserted portion of the endoscope and the object becomes large, but close observations become worse. In contrast, when the condition exceeds the upper limit of the conditional expressions (7) and (8), close observations become better and distant observations become worse.

Also, it is preferable to employ the following conditional expressions (7') and (8') instead of the conditional expressions (7) and (8).

$$0.10 \leq \gamma_S(50) \leq 0.20 \tag{7'}$$

$$0.15 \leq \gamma_W(50) \leq 0.25 \tag{8'}$$

In this embodiment, it is possible to make the amount of light from the illumination optical system 3 having a wide light distribution larger than that of the illumination optical system 2, by making the illumination window of the illumination optical system 3 having the wide light distribution larger than that of the illumination optical system 2, and by locating a light guide having diameter larger than the illumination window of the illumination optical system 2 having the narrow light distribution so that the diameter of the light guide is set in accordance with the light window of the illumination optical system 3 having the wide light distribution.

Since the illumination optical system 3 having a wide light distribution is distant relative to the observation optical system 1, it is possible to provide sufficient illumination to the observation object by making the amount of light radiated by the illumination optical system 3 having the wide light distribution large. Thus, by providing the sufficient amount of light from the illumination optical system 3 which is distant from the observation optical system 1, it becomes possible to conduct better observation when the observation object is located at an adjacent position.

On the other hand, it is also possible to make the amount of light from the illumination optical system 2 having a narrow light distribution than that of the illumination optical system 3, by making the illumination window of the illumination optical system 2 having the narrow light distribution larger than that of the illumination optical system 3, and by locating a light guide having a diameter larger than the illumination window of the illumination optical system 3 having the wide light distribution so that the diameter of the light guide is set in accordance with the light window of the illumination optical system 2 having the narrow light distribution.

By employing this configuration, brightness of long distant observations becomes better, and sufficient brightness becomes available in farther observations.

Figure 2:
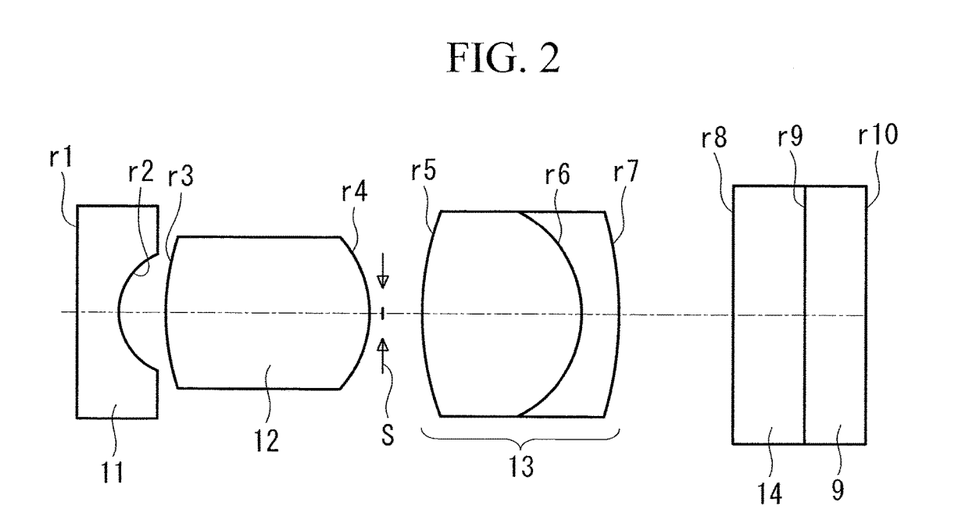
FIG. 2 is a sectional view showing an example of the configuration of an observation optical system of the endoscope according to the embodiment of the present invention.

FIG. 2 is a sectional view showing an example of the configuration of the observation optical system 1 according to this embodiment.

As shown in FIG. 2, the observation optical system. 1 includes a concave lens 11, a convex lens 12, an aperture stop S, a cemented lens 13 having a convex lens and a concave lens, a cover glass 14, and a COD glass 9, which are arranged in the aforementioned order from the object.

Figure 3:
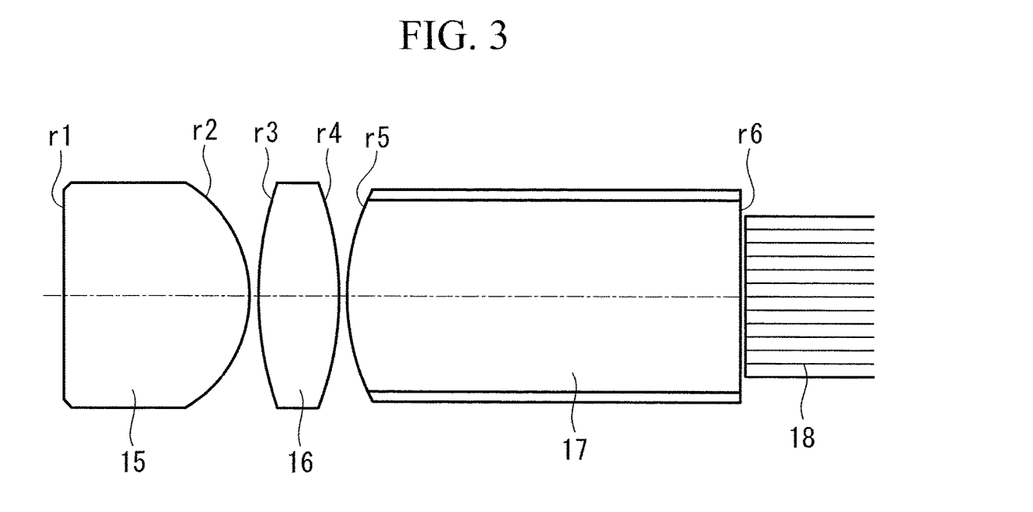
FIG. 3 is a sectional view showing an example of the configuration of an illumination optical system with a wide angle light distribution provided in the endoscope according to the embodiment of the present invention.

As shown in FIG. 3 is a sectional view showing an example of the configuration of the illumination optical system 3 having a wide light distribution according to this embodiment.

As shown in FIG. 3, the illumination optical system 3 having a wide light distribution includes a plano-convex lens 15, a biconvex lens 16, a glass rod 17 consisting of a core and a clad, and a light guide 18 for guiding light radiated from a light source which is not shown in the drawings, which are arranged in the aforementioned order from the object. Further, the illumination optical system 3 has a configuration which can perform a certain light distribution by reflecting light radiated by the light guide 18 by each of the lenses.

As an illumination optical system, it is possible to employ various components which include a component having one convex lens, a component having one concave lens, or a component having two convex lenses. Since having a small number of lenses makes the light distribution narrow, the illumination optical system 3 having a wide light distribution of this embodiment comprises three convex lenses as described above.

Figure 4:
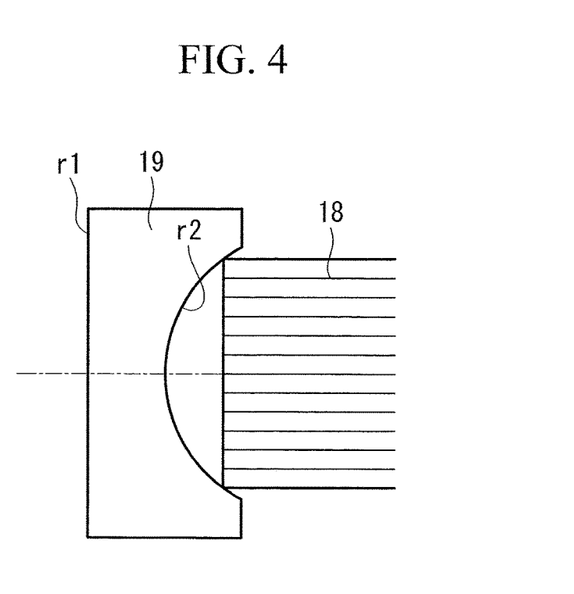
FIG. 4 is a sectional view showing an example of the configuration of an illumination optical system with a narrow angle light distribution provided in the endoscope according to the embodiment of the present invention.

FIG. 4 is a sectional view showing an example of the configuration of the illumination optical system 2 having a narrow light distribution according to this embodiment.

As shown in FIG. 4, the illumination optical system 2 having a narrow light distribution includes a convex lens 19, and a light guide 18 for guiding light radiated from a light source which is not shown in the drawings. With this configuration, it is possible to reduce manufacturing costs by employing a simple configuration.

Note that it is also possible for the illumination optical system 2, which has a narrow light distribution, to comprise three convex lenses as the illumination optical system 3 having a wide light distribution has as described above.

Figure 5:
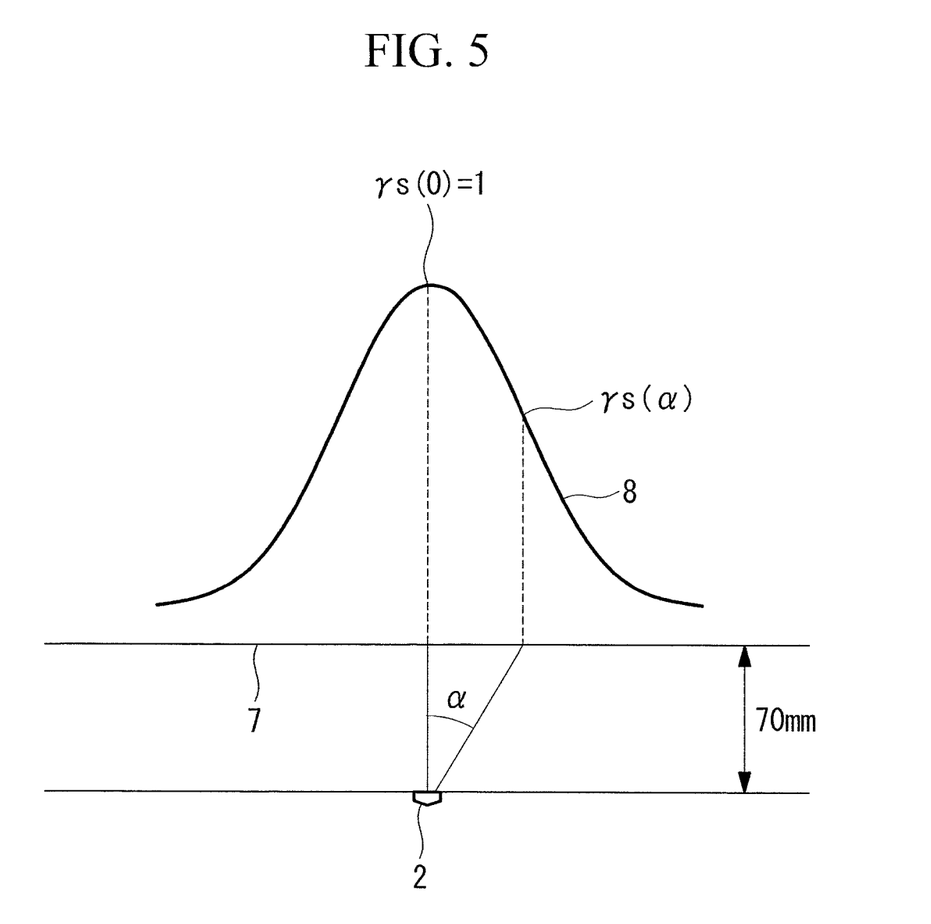
FIG. 5 is a graph showing a light distribution characteristic of the illumination optical system with the narrow angle light distribution provided in the endoscope according to the embodiment of the present invention.

FIG. 5 shows a light distribution characteristic of the illumination optical system 2.

A light distribution characteristic 8 is seen on a flat surface 7 which is 70 mm distant from the illumination optical system 2. At this time, in FIG. 5, when the upward direction in the paper is 0°, the brightness at the 0° position is $\gamma_S(0)=1$, angle $\alpha$ is the angle toward the clockwise direction from the upward direction, and the brightness of the angle is $\gamma_S(0)$. Note that angle $\alpha$ may be the angle toward the counterclockwise direction since the light distribution is symmetrical. Also, the light distribution characteristic $\gamma_W(\alpha)$ can be also considered in the same way as the aforementioned light distribution characteristic of the illumination optical system 2.

Figure 6:
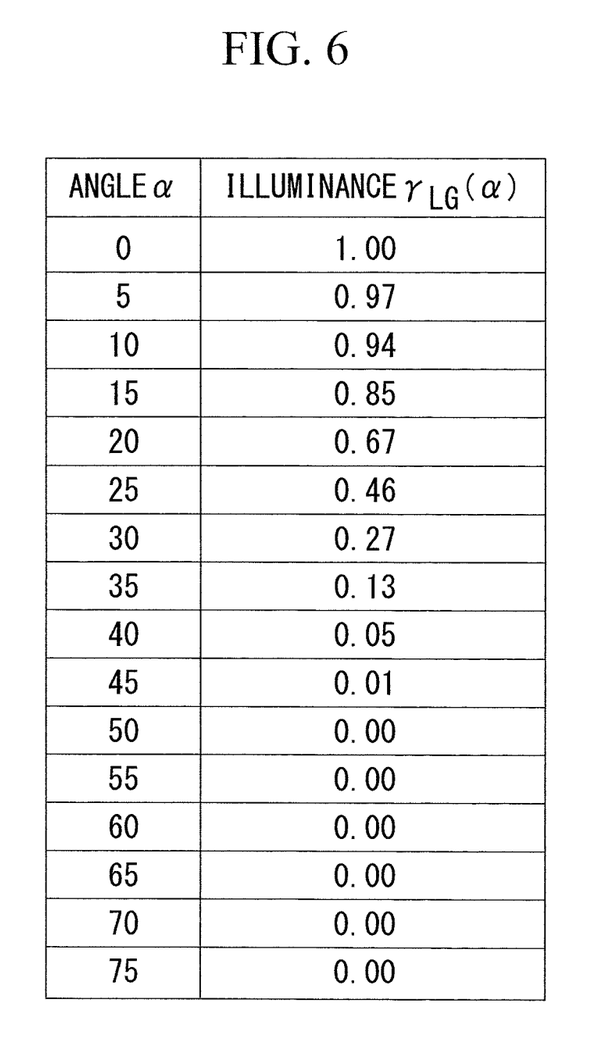
FIG. 6 is a graph showing a light distribution characteristic of a light guide applied in a illumination optical system provided in the endoscope according to the embodiment of the present invention.

Further, FIG. 6 shows a light distribution characteristic $r_{LG}(\alpha)$ of the light guide 18.

As described above, in this embodiment, the illumination optical system 2 having a narrow light distribution is located at a position relatively near the objective optical system 1 and the amount of light from the illumination optical system 2 is small, and the illumination optical system 3 having a wide light distribution is located at a position relatively distant from the objective optical system 1 and the amount of light from the illumination optical system 3 is large. Therefore, it is possible to realize a desired observation, surely obtaining sufficient light distribution and brightness, and preventing flare and halation.

MODIFIED EXAMPLE

Figure 7:
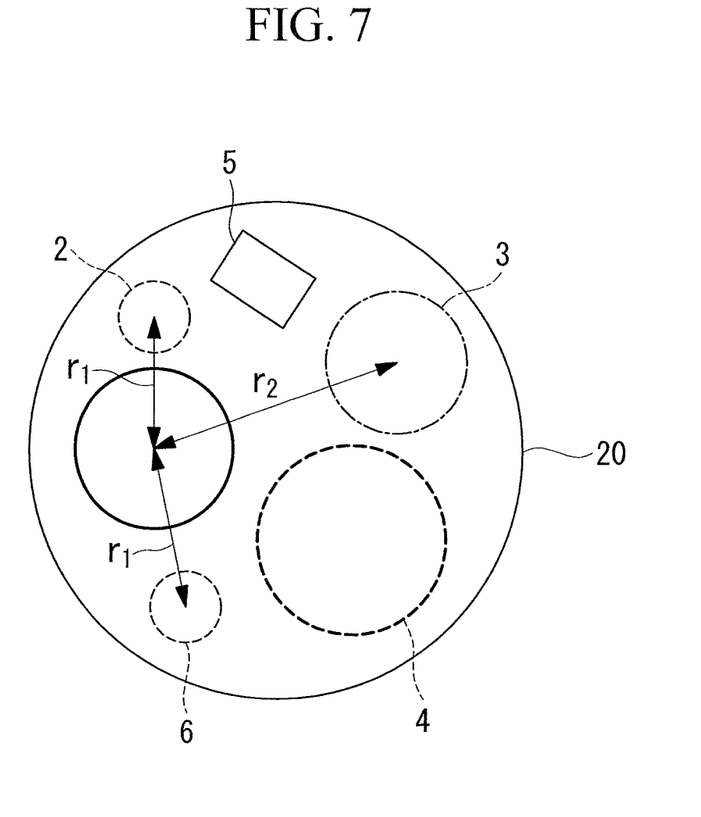
FIG. 7 is a drawing for explanation showing a distal end surface of an inserted portion of an endoscope according a modified example of the embodiment of the present invention.

FIG. 7 shows the configuration of a distal end 20 of the inserted portion of the endoscope according to a modified example of the aforementioned embodiment of the present invention. As shown in FIG. 7, the endoscope according to this modified example may have three illumination optical systems 2, 3, 6 as the illumination optical system. In the endoscope of this modified embodiment, the same configurations as the aforementioned embodiment are accompanied with the same reference signs, and the explanations thereof are omitted.

In this modified example, the illumination optical system 2 and the illumination optical system 6 are the illumination optical systems having the same configuration, and have a narrower light distribution than that of the illumination optical system 3. Also, as shown in FIG. 6, the illumination optical systems 2, 6 having narrow light distributions are located at the positions which have the same distance from the objective optical system 1, and the illumination optical system 3 having a wide light distribution is distant from the objective optical system 1 relative to the illumination optical systems 2, 6 having the narrow light distributions. Thus, the illumination optical systems 2, 6 which have narrow light, distributions are located at positions whose distances from the center of the objective optical system 1 are r1, and the illumination optical system 3 which has a wide light distribution is located at a position whose distance from the center is r2 (r1<r2).

Further, when the endoscope according to this modified example is configured to satisfy the aforementioned conditional expressions (1)-(8), it is possible to realize a desired observation, surely obtaining sufficient light distribution and brightness, and preventing flare and halation.

Implemented Examples

Next, implemented examples 1-5 according to either of the aforementioned embodiment or the aforementioned modified example will be described below. In each of the implemented examples, r1 is the distance between the center of the objective optical system and the center of the illumination optical system having a narrow light distribution, r2 is the distance between the center of the objective optical system and the center of the illumination optical system having a wide light distribution, $f_W$ is the focal length of the illumination optical system which has the widest light distribution, $f_S$ is the focal length of the illumination optical system which has the narrowest light distribution, $\phi_W$ is the outer diameter of the lens at a position which is the nearest to the object within the illumination optical system which has the widest light distribution, $\phi_S$ is the outer diameter of the lens at a position which is the nearest to the object within the illumination optical system which has the narrowest light distribution, $f_L$ is the focal length of the objective optical system, $\phi_L$ is the maximum image height of the observation optical system, $\gamma_S(60)$ is a ratio of an amount of radiated light at a radiation angle of 60° of the illumination optical system having the narrowest light distribution relative to the amount of radiated light at the radiation angle of 0° of the illumination optical system having the narrowest light distribution, $\gamma_W(60)$ is a ratio of an amount of radiated light at a radiation angle of 60° of the illumination optical system having the widest light distribution relative to the amount of radiated light at the radiation angle of 0° of the illumination optical system having the widest light distribution, $\gamma_S(50)$ is a ratio of an amount of radiated light at a radiation angle of 50° of the illumination optical system having the narrowest light distribution relative to an amount of radiated light at a radiation angle of 0° of the illumination optical system having the narrowest light distribution, and $\gamma_W(50)$ is a ratio of an amount of radiated light at a radiation angle of 50° of the illumination optical system having the widest light distribution relative to an amount of radiated light at a radiation angle of 0° of the illumination optical system having the widest light distribution.

Also, in the lens data described in each of the implemented examples, r is a radius of curvature (mm), d is a distance between surfaces (mm), Nd is a refractive index for a d line, ν is an Abbe number.

Implemented Example 1

The endoscope according to the implemented example 1 of the present invention has an observation optical system, one illumination optical system having a narrow light distribution, and one illumination optical system having a wide light distribution (See FIG. 1).

The lens data of the observation optical system and the illumination optical systems of the implemented example 1 are shown below.

(Observation optical system)

Lens data

| Surface Number | r | d | Nd | ν |
|---|---|---|---|---|
| 1 | ∞ | 0.339 | 1.883 | 40.8 |
| 2 | 0.642 | 0.390 | 1.670 | 47.3 |
| 3 | 3.205 | 1.656 | 1.729 | 54.7 |
| 4 | −1.170 | 0.050 | 1.923 | 18.9 |
| 5 | ∞ | 0.318 | 1.516 | 64.1 |
| 6 | 3.361 | 1.300 | 1.505 | 63.3 |
| 7 | −1.124 | 0.299 | | |
| 8 | −4.202 | 0.935 | | |
| 9 | ∞ | 0.600 | | |
| 10 | ∞ | 0.500 | | |

Various data

| | |
|---|---|
| $f_L$ | 0.99 |
| $\phi_L$ | 1.00 |

(Illumination optical system having a narrow light distribution)

Lens data

| Surface Number | r | d | Nd |
|---|---|---|---|
| 1 | ∞ | 1.3 | 1.883 |
| 2 | −2.00 | 0.04 | 1.883 |
| 3 | 2.00 | 0.75 | 1.730 |
| 4 | −2.00 | 0.05 | 1.520 |
| 5 | 1.91 | 2.9 | |
| 6 | ∞ | | |

Various data

| | |
|---|---|
| $f_S$ | 0.72 |
| $\phi_S$ | 1.6 |
| $\gamma_S(60)$ | 0.053 |
| $\gamma_S(50)$ | 0.17 |
| Light Guide Diameter $\phi_{LG}$ | 1.38 |
| r1 | 3.4 |

(Illumination optical system having a wide light distribution)

Lens data

| Surface Number | r | d | Nd |
|---|---|---|---|
| 1 | ∞ | 1.6 | 1.883 |
| 2 | −1.53 | 0.06 | 1.883 |
| 3 | 3.97 | 0.74 | 1.730 |
| 4 | −1.90 | 0.12 | 1.520 |
| 5 | 3.62 | 3.4 | |
| 6 | ∞ | | |

Various data

| | |
|---|---|
| $f_W$ | 0.83 |
| $\phi_W$ | 2.05 |
| $\gamma_W(60)$ | 0.062 |
| $\gamma_W(50)$ | 0.18 |
| Light Guide Diameter $\phi_{LG}$ | 1.60 |
| r2 | 4.5 |

Implemented Example 2

The endoscope according to the implemented example 2 of the present invention has an observation optical system, one illumination optical system having a narrow light distribution, and one illumination optical system having a wide light distribution (See FIG. 1).

The lens data of the illumination optical systems of the implemented example 2 are shown below.

Note that the lens data of the observation optical system are the same as those of the implemented example 1, and therefore the lens data thereof is not shown in the following description.

(Illumination optical system having a narrow light distribution)

Lens data

| Surface Number | r | d | Nd |
|---|---|---|---|
| 1 | ∞ | 0.36 | 1.883 |
| 2 | 0.76 | 0.30 | |

Various data

| | |
|---|---|
| $f_S$ | −0.86 |
| $\phi_S$ | 1.60 |
| $\gamma_S(60)$ | 0.025 |
| $\gamma_S(50)$ | 0.11 |
| Light Guide Diameter $\phi_{LG}$ | 1.20 |
| r1 | 3.2 |

(Illumination optical system having a wide light distribution)

Lens data

| Surface Number | r | d | Nd |
|---|---|---|---|
| 1 | ∞ | 1.3 | 1.883 |
| 2 | −2.00 | 0.04 | 1.883 |
| 3 | 2.00 | 0.75 | 1.730 |
| 4 | −2.00 | 0.05 | 1.520 |
| 5 | 1.91 | 2.9 | |
| 6 | ∞ | | |

Various data

| | |
|---|---|
| $f_W$ | 0.72 |
| $\phi_W$ | 1.6 |
| $\gamma_W(60)$ | 0.053 |
| $\gamma_W(50)$ | 0.17 |
| Light Guide Diameter $\phi_{LG}$ | 1.38 |
| r2 | 4.1 |

Implemented Example 3

The endoscope according to the implemented example 3 of the present invention has an observation optical system, one illumination optical system having a narrow light distribution, and one illumination optical system having a wide light distribution (See FIG. 1).

The lens data of the illumination optical systems of the implemented example 3 are shown below.

Note that the lens data of the observation optical system are the same as those of the implemented example 1, and therefore the lens data is thereof not shown in the following description.

(Illumination optical system having a narrow light distribution)

Lens data

| Surface Number | r | d | Nd |
|---|---|---|---|
| 1 | ∞ | 1.72 | 1.883 |
| 2 | −2.76 | 0.06 | 1.883 |
| 3 | 3.97 | 0.74 | 1.730 |
| 4 | −1.90 | 0.12 | 1.520 |
| 5 | 3.62 | 3.4 | |
| 6 | ∞ | | |

Various data

| | |
|---|---|
| $f_S$ | 0.97 |
| $\phi_S$ | 1.95 |
| $\gamma_S(60)$ | 0.05 |
| $\gamma_S(50)$ | 0.16 |
| Light Guide Diameter $\phi_{LG}$ | 1.80 |
| r1 | 3.8 |

(Illumination optical system having a wide light distribution)

Lens data

| Surface Number | r | d | Nd |
|---|---|---|---|
| 1 | ∞ | 1.11 | 1.883 |
| 2 | −1.01 | 0.04 | 1.883 |
| 3 | 1.20 | 0.65 | 1.805 |
| 4 | ∞ | 0 | 1.520 |
| 5 | 1.26 | 2.75 | |
| 6 | ∞ | | |

Various data

| | |
|---|---|
| $f_W$ | 0.54 |
| $\phi_W$ | 1.2 |
| $\gamma_W(60)$ | 0.053 |
| $\gamma_W(50)$ | 0.18 |
| Light Guide Diameter $\phi_{LG}$ | 1.10 |
| r2 | 4.6 |

Implemented Example 4

The endoscope according to the implemented example 4 of the present invention has an observation optical system, two illumination optical systems each having a narrow light distribution, and one illumination optical system having a wide light distribution (See FIG. 7).

The lens data of the observation optical system and the illumination optical systems of the implemented example 4 are shown below.

(Observation optical system)

Lens data

| Surface Number | r | d | Nd | ν |
|---|---|---|---|---|
| 1 | ∞ | 0.291 | 1.883 | 40.8 |
| 2 | 0.648 | 0.516 | 1.652 | 58.5 |
| 3 | 2.138 | 1.549 | 1.589 | 61.2 |
| 4 | −1.213 | 0.050 | 1.923 | 18.9 |
| 5 | ∞ | 0.402 | 1.516 | 64.1 |
| 6 | 1.643 | 1.097 | 1.505 | 63.3 |

-continued (Observation optical system)

| | | |
|---|---|---|
| 7 | −1.013 | 0.299 |
| 8 | −4.783 | 0.573 |
| 9 | ∞ | 0.500 |
| 10 | ∞ | 0.400 |

Various data

| | |
|---|---|
| $f_L$ | 0.91 |
| $\phi_L$ | 0.85 |

(Illumination optical system having a narrow light distribution)

Lens data

| Surface Number | r | d | Nd |
|---|---|---|---|
| 1 | ∞ | 1.11 | 1.883 |
| 2 | −1.01 | 0.04 | 1.883 |
| 3 | 1.20 | 0.65 | 1.805 |
| 4 | ∞ | 0 | 1.520 |
| 5 | 1.26 | 2.75 | |
| 6 | ∞ | | |

Various data

| | |
|---|---|
| $f_S$ | 0.54 |
| $\phi_S$ | 1.2 |
| $\gamma_S(60)$ | 0.053 |
| $\gamma_S(50)$ | 0.18 |
| Light Guide Diameter $\phi_{LG}$ | 1.10 |
| r1 | 3.2 |

(Illumination optical system having a wide light distribution)

Lens data

| Surface Number | r | d | Nd |
|---|---|---|---|
| 1 | ∞ | 1.3 | 1.883 |
| 2 | −2.00 | 0.04 | 1.883 |
| 3 | 2.00 | 0.75 | 1.730 |
| 4 | −2.00 | 0.05 | 1.520 |
| 5 | 1.91 | 2.9 | |
| 6 | ∞ | | |

Various data

| | |
|---|---|
| $f_W$ | 0.63 |
| $\phi_W$ | 1.2 |
| $\gamma_W(60)$ | 0.081 |
| $\gamma_W(50)$ | 0.22 |
| Light Guide Diameter $\phi_{LG}$ | 1.38 |
| r2 | 5.3 |

The endoscope according to the implemented example 5 of the present invention has one illumination optical system having a narrow light distribution and one illumination optical system having a wide light distribution.

The lens data of the illumination optical systems of the implemented example 5 are shown below.

Note that the lens data of the observation optical system are the same as those of the implemented example 1, and therefore the lens data thereof is not shown in the following description.

(Illumination optical system having a narrow light distribution)

Lens data

| Surface Number | r | d | Nd |
|---|---|---|---|
| 1 | ∞ | 0.36 | 1.883 |
| 2 | 0.76 | 0.30 | |

Various data

| | |
|---|---|
| $f_S$ | −0.86 |
| $\phi_S$ | 1.60 |
| $\gamma_S(60)$ | 0.025 |
| $\gamma_S(50)$ | 0.11 |
| Light Guide Diameter $\phi_{LG}$ | 1.20 |
| r1 | 4.0 |

(Illumination optical system having a wide light distribution)

Lens data

| Surface Number | r | d | Nd |
|---|---|---|---|
| 1 | ∞ | 1.3 | 1.883 |
| 2 | −2.00 | 0.04 | 1.883 |
| 3 | 2.00 | 0.75 | 1.730 |
| 4 | −2.00 | 0.05 | 1.520 |
| 5 | 1.91 | 2.9 | |
| 6 | ∞ | | |

Various data

| | |
|---|---|
| $f_W$ | 0.63 |
| $\phi_W$ | 1.2 |
| $\gamma_W(60)$ | 0.081 |
| $\gamma_W(50)$ | 0.22 |
| Light Guide Diameter $\phi_{LG}$ | 1.38 |
| r2 | 5.8 |

The values related to the conditional expressions (1)-(8) of the implemented examples 1-5 are shown in the following table 1.

TABLE 1

| CONDITIONAL EXPRESSION | IMPLEMENTED EXAMPLE 1 | IMPLEMENTED EXAMPLE 2 | IMPLEMENTED EXAMPLE 3 | IMPLEMENTED EXAMPLE 4 | IMPLEMENTED EXAMPLE 5 |
|---|---|---|---|---|---|
| (1) | 0.90 | 0.85 | 0.90 | 0.88 | 0.73 |
| (2) | 2.19 | 1.85 | 2.00 | 2.39 | 2.00 |
| (3) | 1.32 | 1.28 | 1.21 | 1.66 | 1.45 |
| (4) | 19.3 | 16.5 | 27.8 | 30.3 | 29.8 |
| (5) | 33.7 | 27.2 | 40.7 | 83.2 | 62.6 |
| (6) | 1.17 | 2.12 | 1.06 | 1.53 | 3.24 |
| (7) | 0.17 | 0.11 | 0.16 | 0.18 | 0.11 |
| (8) | 0.18 | 0.17 | 0.18 | 0.22 | 0.22 |

The inventors have arrived at the following aspects of the invention.

One aspect of the present invention provides an endoscope comprising: an observation optical system provided in a distal end of an inserted portion of the endoscope, for observation of an object; and a plurality of illumination optical systems which are provided in the inserted portion and which direct illumination light radiated from a light source toward the object so that the same angle of view is irradiated by the plurality of illumination optical systems, wherein one of the illumination optical systems which has the widest light distribution is distant from the observation optical system relative to another one of the illumination optical systems which has the narrowest light distribution, and the following conditional expression is satisfied.

$$0.6 \leq |\phi_S \cdot f_W / \phi_W \cdot f_S| \leq 1.0 \tag{1}$$

In the expression, $f_W$ is a focal length of the illumination optical system which has the widest light distribution, $f_S$ is a focal length of the illumination optical system which has the narrowest light distribution, $\phi_W$ is an outer diameter of a lens at a position which is the nearest to the object within the illumination optical system having the widest light distribution, and $\phi_S$ is an outer diameter of lens at a position which is the nearest to the object within the illumination optical system having the narrowest light distribution.

According to this aspect, when the conditional expression (1) is satisfied, it becomes possible to realize a desired observation, making the amount of light large, surely obtaining sufficient light distribution, and preventing flare and halation.

When the condition exceeds the upper limit of the conditional expression (1), the light distribution at a position near the observation optical system becomes wide, and undesirable phenomena, such as flare and halation tend to occur. On the other hand, the condition does not reach the lower limit of the conditional expression (1), since one of the light distributions becomes undesirably wide, only the position where the illumination is located becomes bright, and unevenness arises by the illumination optical system in a state in which a portion of the image is bright, while it is suitable regarding flare and halation.

The reason why satisfying the conditional expression (1) is required is as follows. In general, when the amount of light from the illumination optical system is large or its light distribution is wide, flare caused by light directly going into the objective optical system or halation that part of an observation image becomes too white because of strong light irradiated on the periphery when approaching to the object, caused by a situation where the amount of light at the periphery becomes large, and the like, which are optically undesirable phenomena, are caused frequently. Thus, in order to achieve illumination with less flare and halation with regard to the illumination optical system disposed at a position near the objective optical system, it is necessary to make the amount of light from the illumination optical system small, and to make the light distribution relatively narrow. In other words, it is necessary to make the focal length long, and to make the outer diameter of the lens small.

However, when the aforementioned configuration is employed, the amount of light at a distant point becomes insufficient, and therefore the light distribution at the periphery of the image becomes insufficient. Thus, it is necessary to make the amount of light from the illumination optical system, which is located at the distant side in the plurality of illumination optical systems, large, and to make the light distribution wide. In other words, the focal length should be shortened, and the outer diameter of the lens should be enlarged. Thus, it is necessary to satisfy the conditional expression (1) in order to achieve the aforementioned two configurations.

In the above-described aspect, it is preferable to employ the following conditional expression (1') instead of the conditional expression (1), and also it is more preferable to employ the following conditional expression (1") instead of the conditional expression (1').

$$0.7 \leq |\phi_S \cdot f_W / \phi_W \cdot f_S| \leq 0.95 \tag{1'}$$

$$0.75 \leq |\phi_S \cdot f_W / \phi_W \cdot f_S| \leq 0.92 \tag{1"}$$

In the above-described aspect, the following conditional expression may be employed.

$$1.6 \leq |\phi_S \cdot f_L / f_S \cdot \phi_L| \leq 2.8 \tag{2}$$

In the expression, $f_L$ is a focal length of the objective optical system, and $\phi_L$ is a maximum image height of the observation optical system.

When the conditional expression (2) is satisfied, illumination suitable for close observation may be realized. When the condition does not reach the lower limit of the conditional expression (2), it becomes impossible to conduct a desired observation due to undesirably narrow light distribution of the illumination optical system and undesirably wide field of view of the observation optical system. When the condition exceeds the upper limit of the conditional expression (2), the field of view becomes too narrow, which is not desirable.

The reason why satisfying the conditional expression (2) is required is as follows. When observation is performed in a close manner, the effect of the illumination optical system located at a distant position relative to the observation optical system becomes weak, and the effect of the illumination optical system located at a close position relative to the observation optical system becomes large. Also, since the object generally tends to have a planer body when a close observation is performed, the observation becomes difficult due to directly reflected light from the object, and it becomes necessary to set the illumination optical system 2 in a proper way. Further, when approaching to the object, necessary irradiated area is largely influenced by the observation area which depends on the field of view of the observation optical system. For the reasons above, in order to provide an illumination optical system especially suitable for close observation, it is necessary for the illumination optical system and the observation optical system to satisfy the conditional expression (2).

It is preferable to employ the following conditional expression (2') instead of the conditional expression (2), and also it is more preferable to employ the following conditional expression (2") instead of the conditional expression (2').

$$1.8 \leq |\phi_S \cdot f_L / f_S \cdot \phi_L| \leq 2.6 \tag{2'}$$

$$2.0 \leq |\phi_S \cdot f_L / f_S \cdot \phi_L| \leq 2.4 \tag{2"}$$

In the above-described aspect, the following conditional expression may be employed.

$$1.0 \leq r_2 / r_1 \leq 2.0 \tag{3}$$

In the expression, $r_1$ is a distance between a center of the observation optical system and a center of the illumination optical system having a narrow light distribution, and $r_2$ is a distance between a center of the observation optical system and a center of the illumination optical system having a wide light distribution.

When the conditional expression (3) is satisfied, the brightness at the time of close observation becomes even over the entire observation area, and thereby a better observation becomes available. When the condition does not reach the lower limit of the conditional expression (3), only the direction to which the illumination having the wide light distribution is positioned is brightly irradiated, and thereby the brightness does not become even over the entire observation area. When the condition exceeds the upper limit of the conditional expression (3), it leads to an undesirable situation where the brightness is not even over the entire observation area.

The reason why satisfying the conditional expression is required is as follows. When the plurality of illumination optical systems, each of which has a light distribution different from each other, are located, by positioning the illumination optical system having a wide light distribution so that the illumination optical system is positioned farther relative to the observation optical system than the other illumination optical system, it becomes possible to conduct a desired observation because the brightness at the time of close observation becomes even over the entire observation area, compared with a situation where the illumination optical systems are positioned at the same distance from the observation optical system. Therefore, it is preferable that the conditional expression (3) is satisfied.

It is more preferable to employ the following conditional expression (3') instead of the conditional expression (3).

$$1.2 \leq r_2/r_1 \leq 1.8 \tag{3'}$$

In the above-described aspect, the following conditional expressions may be employed.

$$12 \leq r_1^2/|f_S \cdot f_W| \leq 48 \tag{4}$$

$$24 \leq r_2^2/|f_S \cdot f_W| \leq 96 \tag{5}$$

When the conditional expressions (4) and (5) are satisfied, it becomes possible to conduct a desired observation. In both of the conditional expressions (4) and (5), when the condition does not reach each of the lower limits, since the light distribution becomes too wide, frequency of causing undesired phenomena, such as flare and halation, becomes high. On the other hand, when the condition exceeds each of the upper limits in the conditional expressions (4) and (5), the illumination optical system is located at a position which is distant from the objective optical system, and thereby sufficient light does not reach the observation area, or it becomes impossible to ensure sufficient brightness because of too narrow light distribution of the illumination optical systems.

The reason why satisfying the conditional expressions (4) and (5) is required is as follows. In general, when trying to reduce halation, there is a fear that light distribution tends to be insufficient. Especially, when the distance between the observation optical system and the illumination optical systems is changed, the influence also changes. Thus, with regard to the illumination optical systems, it is desirable that the light distributions of them are respectively and appropriately set in accordance with the distances between the objective observation system and the illumination observation systems. Thus, in order to achieve a desired observation, it is preferable that the conditional expressions (4) and (5) are satisfied.

The above-described aspect can be configured so that angle characteristics of the illumination optical system having the narrowest light distribution and the illumination optical system having the widest light distribution satisfy the following conditional expression.

$$\gamma_W(60)/\gamma_S(60) \geq 1.0 \tag{6}$$

In, the expression, $\gamma_S(60)$ is a ratio of an amount of radiated light at a radiation angle of 60° of the illumination optical system having the narrowest light distribution relative to the amount of radiated light at the radiation angle of 0° of the illumination optical system having the narrowest light distribution, and $\gamma_W(60)$ is a ratio of an amount of radiated light at a radiation angle of 60° of the illumination optical system having the widest light distribution relative to the amount of radiated light at the radiation angle of 0° of the illumination optical system having the widest light distribution.

When the conditional expression (6) is satisfied, it becomes possible to ensure sufficient brightness at the periphery in close observation. In other words, since light from the illumination optical system located at a distant position is sufficiently irradiated onto the observation area at the time of close observation, balanced brightness can be ensured, without unevenness.

It is preferable to employ the following conditional expression (6') instead of the conditional expression (6), and also it is more preferable to employ the following conditional expression (6") instead of the conditional expression (6').

$$\gamma_W(60)/\gamma_S(60) \geq 1.15 \tag{6'}$$

$$\gamma_W(60)/\gamma_S(60) \geq 1.50 \tag{6''}$$

The above-described aspect can be configured so that the angle characteristics of the illumination optical system having the narrowest light distribution and the illumination optical system having the widest light distribution satisfy the following conditional expression.

$$0.05 \leq \gamma_S(50) \leq 0.25 \tag{7}$$

$$0.10 \leq \gamma_W(50) \leq 0.30 \tag{8}$$

In the expression, $\gamma_S(50)$ is a ratio of an amount of radiated light at a radiation angle of 50° of the illumination optical system having the narrowest light distribution relative to an amount of radiated light at a radiation angle of 0° of the illumination optical system having the narrowest light distribution, and $\gamma_W(50)$ is a ratio of an amount of radiated light at a radiation angle of 50° of the illumination optical system having the widest light distribution relative to an amount of radiated light at a radiation angle of 0° of the illumination optical system having the widest light distribution.

When the conditional expressions (7) and (8) are satisfied, desired observation can be performed even when the distal end of the inserted portion of the endoscope and the object are distant from each other with a certain degree.

When the condition does not reach the lower limit of the conditional expressions (7) and (8), observations become better when the distance between the distal end of the inserted portion of the endoscope and the object becomes large, but close observations become worse. In contrast, when the condition exceeds the upper limit of the conditional expressions (7) and (8), close observations become better and distant observations become worse.

It is preferable to employ the following conditional expressions (7') and (8') instead of the conditional expressions (7) and (8).

$$0.10 \leq \gamma_S(50) \leq 0.20 \tag{7'}$$

$$0.15 \leq \gamma_W(50) \leq 0.25 \tag{8'}$$

The above-described aspect can be configured so that the amount of radiated light from the illumination optical system having the widest light distribution in the plurality of illumination optical systems is larger than the amount of radiated light from the illumination optical system having the narrowest light distribution, and the illumination optical system having the widest light distribution is more distant from the observation optical system relative to the illumination, optical system having the narrowest light distribution.

In a case where the illumination optical system having a wide light distribution is located at a position distant relative to the observation optical system, in order to realize a desired observation at the time of close observation, it is preferable that light radiated from the illumination optical system having the wide light distribution is large. Thus, when the illumination optical system having the wide light distribution is located at the distant position, it is possible to supply a sufficient amount of light to the observation area which is located at a close position, by making the amount of irradiated light large.

The above-described aspect can be configured so that the amount of radiated light from the illumination optical system having the widest light distribution in the plurality of illumination optical systems is smaller than the amount of radiated light from the illumination optical system having the narrowest light distribution, and the illumination optical system having the widest light distribution is more distant from the observation optical system relative to the illumination optical system having the narrowest light distribution.

When performing distant observations in which the distal end of the inserted portion of the endoscope and the object are distant to a certain degree, desired observation can be realized when the amount of light radiated from the illumination optical system having a narrow light distribution is large. Thus, it is possible to enable desired distant observations by reducing the amount of light radiated from the illumination optical system having a wide light distribution.

Advantageous Effects of Invention

The aforementioned aspects afford an advantage in that a desired observation can be realized, surely obtaining sufficient light distribution and brightness, and preventing flare and halation.

REFERENCE SIGNS LIST

1 observation optical system
2 illumination optical system having a narrow light distribution
3 illumination optical system having a wide light distribution
4 channel
5 nozzle
6 illumination optical system having a narrow light distribution
10 distal end surface of inserted portion of endoscope

What is claimed is:
1. An endoscope comprising:
an observation optical system provided in a distal end of an inserted portion of the endoscope, for observation of an object; and
a plurality of illumination optical systems which are provided in the inserted portion and which direct illumination light radiated from a light source toward the object so that a same angle of view is irradiated by the plurality of illumination optical systems, wherein one of the illumination optical systems which has the widest light distribution is distant from the observation optical system relative to another one of the illumination optical systems which has the narrowest light distribution, and the illumination optical system having the narrowest light distribution and the illumination optical system having the widest distribution satisfy the following conditional expressions (1), (7) and (8),

$$0.6 \leq |\phi_S \cdot f_W / \phi_W \cdot f_S| \leq 1.0 \quad (1)$$

$$0.05 \leq \gamma_S(50) \leq 0.25 \quad (7)$$

$$0.10 \leq \gamma_W(50) \leq 0.30 \quad (8)$$

wherein $f_W$ is a focal length of the illumination optical system which has the widest light distribution, $f_S$ is a focal length of the illumination optical system which has the narrowest light distribution, $\phi_W$ is an outer diameter of a lens at a position which is the nearest to the object within the illumination optical system having the widest light distribution, $\phi_S$ is an outer diameter of a lens at a position which is the nearest to the object within the illumination optical system having the narrowest light distribution, $\gamma_S(50)$ is a ratio of an amount of radiated light at a radiation angle of 50° of the illumination optical system having the narrowest light distribution relative to an amount of radiated light at a radiation angle of 0° of the illumination optical system having the narrowest light distribution, and $\gamma_W(50)$ is a ratio of an amount of radiated light at a radiation angle of 50° of the illumination optical system having the widest light distribution relative to an amount of radiated light at a radiation angle of 0° of the illumination optical system having the widest light distribution.

2. The endoscope according to claim 1, wherein the following conditional expression is satisfied, $$1.6 \leq |\phi_S \cdot f_L / f_S \cdot \phi_L| \leq 2.8 \quad (2)$$

wherein $f_L$ is a focal length of the objective optical system, and $\phi_L$ is a maximum image height of the observation optical system.

3. The endoscope according to claim 1, wherein the following conditional expression is satisfied, $$1.0 \leq r_2/r_1 \leq 2.0 \quad (3)$$

wherein $r_1$ is a distance between a center of the observation optical system and a center of the illumination optical system having the narrowest light distribution, and $r_2$ is a distance between a center of the observation optical system and a center of the illumination optical system having the widest light distribution.

4. The endoscope according to claim 3, wherein the following conditional expressions are satisfied, $$12 \leq r_1^2 / |f_S \cdot f_W| \leq 48 \quad (4)$$

$$24 \leq r_2^2 / |f_S \cdot f_W| \leq 96 \quad (5).$$

5. The endoscope according to claim 4, wherein the following conditional expression is satisfied, $$\gamma_W(60)/\gamma_S(60) \geq 1.0 \quad (6)$$

wherein $\gamma_S(60)$ is a ratio of an amount of radiated light at a radiation angle of 60° of the illumination optical system having the narrowest light distribution relative to the amount of radiated light at the radiation angle of 0° of the illumination optical system having the narrowest light distribution, and $\gamma_W(60)$ is a ratio of an amount of radiated light at a radiation angle of 60° of the illumination optical system having the widest light distribution relative to the amount of radiated light at the radiation angle of 0° of the illumination optical system having the widest light distribution.

6. The endoscope according to claim 1, wherein the amount of radiated light from the illumination optical system having the widest light distribution in the plurality of illumination optical systems is larger than the amount of radiated light from the illumination optical system having the narrowest light distribution, and the illumination optical system having the widest light distribution is more distant from the observation optical system relative to the illumination optical system having the narrowest light distribution.

7. The endoscope according to claim 1, wherein the amount of radiated light from the illumination optical system having the widest light distribution in the plurality of illumination optical systems is smaller than the amount of radiated light from the illumination optical system having the narrowest light distribution, and the illumination optical system having the widest light distribution is more distant from the observation optical system relative to the illumination optical system having the narrowest light distribution.

* * * * *